United States Patent [19]

Imanari et al.

[11] Patent Number: 4,659,841

[45] Date of Patent: Apr. 21, 1987

[54] PROCESS FOR THE PREPARATION OF INDOLES

[75] Inventors: Makoto Imanari; Hiroshi Iwane; Katsufumi Kuzira; Takatoshi Seto, all of Ibaraki, Japan

[73] Assignee: Research Association for Utilization of Light Oil, Tokyo, Japan

[21] Appl. No.: 751,865

[22] Filed: Jul. 5, 1985

[30] Foreign Application Priority Data

Jul. 10, 1984 [JP] Japan .............................. 59-142783
Mar. 19, 1985 [JP] Japan .............................. 60-55460

[51] Int. Cl.$^4$ .......................................... C07D 209/08
[52] U.S. Cl. .................................... 548/508; 548/505
[58] Field of Search ........................................ 548/508

[56] References Cited

U.S. PATENT DOCUMENTS 4,436,917 3/1984 Matsuda et al. ..................... 548/508

OTHER PUBLICATIONS

Japio Abstract of Japanese OPI 46865 published 04/28/81.
Japio Abstract of Japanese OPI 109471, published 06/29/83.
Japio Abstract of Japanese OPI 169668, published 12/26/81.
Japio Abstract of Japanese OPI 121270 published 07/19/1983.
Japio Abstract of Japanese OPI 110672 published 09/01/81.
Japio Abstract of Japanese OPI 73060 published 06/17/81.
Japio Abstract of Japanese OPI 55366 published 05/15/81.
Japio Abstract of Japanese OPI 36451 published 04/09/81.
Japio Abstract of Japanese OPI 53652 published 05/13/81.
Japio Abstract of Japanese OPI 225062 published 12/27/83.
Japio Abstract of Japanese OPI 46067 published 03/17/81.

*Primary Examiner*—Mary E. Ceperley
*Attorney, Agent, or Firm*—Oblon, Fisher, Spivak, McClelland & Maier

[57] ABSTRACT

A process for preparing indoles in high yield by reacting anilines and 1,2-glycols in a liquid phase in the presence of a cadmium bromide or iodide/potassium bromide or iodide catalyst. The used catalyst can be easily recovered and when reused, exhibits excellent performance.

25 Claims, No Drawings

PROCESS FOR THE PREPARATION OF INDOLES

FIELD OF THE INVENTION

The present invention relates to a process for the preparation of indoles, and more particularly, to a process for preparing indoles by catalytic reaction of anilines and 1,2-glycols.

BACKGROUND OF THE INVENTION

Indoles are industrially useful substances as a starting material for the preparation of perfumes, amino acids such as tryptophane, and stabilizers for high polymers. It is known that indoles are prepared by reacting anilines and 1,2-glycols in the presence of a catalyst. Various catalysts have been proposed for this purpose, including a dehydrogenation catalyst containing Cu, Cr, Co, Fe, Ni, Zn, Mn, Al, Ca, Pd, Pt, Rh, etc., which are commonly used in the dehydrogenation of alcohols (Japanese Patent Application (OPI) No. 36451/81 (the term "OPI" as used herein means a "published unexamined Japanese patent application")), a cadmium sulfate and/or zinc sulfate-containing catalyst (Japanese Patent Application (OPI) No. 53652/81), a cadmium chloride and/or zinc chloride-containing catalyst (Japanese Patent Application (OPI) No. 46865/81), a copper-containing catalyst (Japanese Patent Application (OPI) No. 55366/81), a cadmium sulfide and/or zinc sulfide-containing catalyst (Japanese Patent Application (OPI) No. 169668/81), a cadmium chloride catalyst (Japanese Patent Application (OPI) No. 109471/83, a calcium sulfate-containing catalyst (Japanese Patent Application (OPI) No. 121270/83), and a silver oxide-containing catalyst (Japanese Patent Application (OPI) No. 225062/83).

In addition, Japanese Patent Application (OPI) No. 46067/83 discloses a method in which the catalyst reaction of anilines and 1,2-glycols is carried out in the presence of water and hydrogen. It is described that numerous catalysts can be used in this method and as one of the catalysts, cadmium halide is disclosed. However, there can be found no description that cadmium iodide can be acutally used nor experiment demonstrating that cadmium iodide can be used.

The above known methods except for those of Japanese Patent Application (OPI) Nos. 46067/83 and 109471/83 are all limited to a gas-phase reaction. In the methods of Japanese Patent Application (OPI) Nos. 46067/83 and 109471/83, it is disclosed that any of gas-phase, liquid-phase, and gas/liquid mixed-phase reactions can be employed. In fact, however, the concrete examples disclosed therein are all directed to the gas-phase reaction, and thus it is not evident whether or not the liquid-phase reaction can be employed.

Japanese Patent Application (OPI) Nos. 73060/81 and 110672/81 disclose a process for preparing indoles in the liquid phase using a catalyst containing a metal of Group VIII in the Periodic Table, magnesium oxide, and the like. However, the results of our experiments on the prior art showed that the process of our experiments on the prior art showed that the process is unsatisfactory for industrial use since large amounts of by-products are formed and the yield is not sufficiently high.

Known catalysts for use in the preparation of indoles by the gas-phase reaction have various disadvantages. For example, their catalyst activity is seriously decreased during the reaction. For the recovery of catalytic activity, therefore, it is necessary to frequently apply a complicated catalyst regeneration operation. Some catalysts cannot be regenerated and activated. Silver-containing catalysts are expensive. Therefore, these catalysts are unsuitable for practical use from a viewpoint of production costs.

SUMMARY OF THE INVENTION

The present invention is intended to overcome the above problems and an object of the present invention is to provide a process whereby the desired indoles can be prepared in high yield, and the used catalyst can be easily recovered, which when reused, exhibits excellent performance.

The present invention provides a process for preparing indoles by reacting anilines and 1,2-glycols in a liquid phase in the presence of a catalyst, wherein the catalyst comprises $CdX_2^1$ and $KX^2$ (wherein $X^1$ and $X^2$, which is the same or different, each represents bromine or iodine).

DETAILED DESCRIPTION OF THE INVENTION

The anilines as used herein are represented by the following general formula (I):

wherein $R^1$ represents a hydrogen atom, an alkyl group having 1 to 4 carbon atoms, an alkoxy group having 1 to 4 carbon atoms, a hydroxy group, a halogen atom, or a nitro group, and $R^2$ represents a hydrogen atom or an alkyl group having 1 to 4 carbon atoms.

Suitable examples of the anilines of the general formula (I) include aniline, o-toluidine, m-toluidine, p-toluidine, o-aminophenol, m-aminophenol, p-aminophenol, o-anisidine, m-anisidine, p-anisidine, o-chloroaniline, m-chloroaniline, p-chloroaniline, o-nitroaniline, m-nitroaniline, and p-nitroaniline.

The 1,2-glycols as used herein are dihydric alcohols represented by the general formula (II):

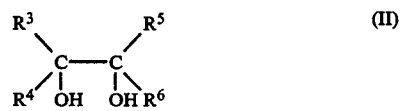

wherein $R^3$, $R^4$, $R^5$ and $R^6$, which are the same or different, each represents a hydrogen atom or an alkyl group having 1 to 4 carbon atoms, which may be substituted with a halogen atom, a hydroxy group, or a cyano group.

Suitable examples of the 1,2-glycols of the general formula (II) include ethylene glycol, propylene glycol, 1,2-butanediol, 2,3-butanediol, pinacol, glycerol, glycerol-2-monochlorohydrin, and glycerol-2-monocyanhydrin.

When ethylene glycol is used as the 1,2-glycol, polyethylene glycols such as diethylene glycol can be added as far as it does not exert adverse influences on the yield of the desired indoles. For example, it can be added in an amount of 50 wt% or less based on the weight of the ethylene glycol.

When o-toluidine is used as the aniline and ethylene glycol is used as the 1,2-glycol, 7-methylindole is formed as the desired indole. When p-aminophenol is used as the aniline, 5-hydroxyindoles are formed.

The catalyst that is used in the process of the present invention is a combination of cadmium bromide and/or cadmium ($CdX_2^1$) and potassium bromide and/or potassium iodide ($KX^2$). The mole ratio of $KX^2$ to $CdX_2^1$ ($KX^2/CdX_2^1$) is 0.1:1 to 10:1, preferably 1:1 to 7:1, and more preferably 2:1 to 5:1.

The cadmium compound ($CdX_2^1$) and the potassium compound ($KX^2$) may be added separately, or as a compound represented by the formula $K_aCdX_{(2+a)}$ (wherein X is bromine and/or iodine, and a is an integer of 1 to 4) which has been previously prepared from the cadmium and potassium compounds.

Various additives can be added to the catalyst of the present invention in amounts not exerting serious adverse influences on the yield of indole. Examples of such additives include the halides, sulfides, sulfates, oxides, etc. of metals such as B, Al, In, Sn, Ti, V, Cr, Si, Mn, Fe, Co, Ni, Cu, Zn, Zr, Mo, Ru, Rh, Pd, Ag, Re, Os, Ir, Pt, Hg, La, Ce, Nd, Na, Li, Rb, Cs, Be, Mg, Ca, Sr, Ba, Pb, Tl, Bi, and Ge, and activated carbon.

The catalyst of the present invention may be used as it is or in the form that it is deposited on a support by usual techniques. Supports commonly used in the preparation of deposited catalysts can be used. Examples of such supports include alumina, silica, activated carbon, silica/alumina, silica gel, activated clay, diatomaceous earth, and pumice.

The process of the present invention is carried out in a liquid phae. This liquid-phase reaction can be carried out in the presence of a diluent or in the absence of a diluent. As these diluents, any compounds which are liquid under reaction conditions can be used as long as they do not exert adverse influences on the reaction. The diluents may be solvents or non-solvents. Suitable examples of these diluents include saturated hydrocarbons such as paraffin and naphthene, aromatic hydrocarbons such as benzene, toluene, and xylene, trialkylamines such as trimethylamine, and organic solvents such as triphenylamine, dioxane, dimethylformamide, dimethyl sulfoxide, pyridine, and N-methylpyrrolidone.

It is preferred that the process of the present invention be carried out in the presence of diluents having a boiling point higher than those of the desired indoles to be prepared. When the used catalyst is recovered and reused after the liquid-phase reaction, the diluent prevents the deposition of the catalyst. In this case, therefore, the use of the diluent is very advantageous from an industrial standpoint. As such diluents, liquid saturated hydrocarbons are preferably used since the yield of indole is greatly increased.

Suitable examples of liquid saturated hydrocarbons having a boiling point higher than that of the desired indoles to be prepared include liquid paraffins. These liquid paraffins need not satisfy the requirements defined in the JIS Standards or Japanese Pharmacopoeia. They may contain small amounts of, e.g., sulfur, polynuclear aromatic hydrocarbon, and olefins. It suffices that they have a boiling point higher than that of the indoles to be prepared. It is preferred that the saturated hydrocarbons contained in these liquid paraffins have a narrow boiling point distribution.

The weight ratio of the liquid saturated hydrocarbons to the anilines as the starting material is usually 0.01:1 to 100:1 and preferably 0.1:1 to 10:1.

The liquid-phase reaction of the present invention can be carried out in either of batchwise and non-batchwise or continuous reaction apparatuses. The reaction can be carried out under superatmospheric or at atmospheric pressure, or under reduced pressure. It is preferred that the reaction be carried out at atmospheric pressure or under superatmospheric pressure, e.g., at a pressure of 0 to 200 kg/cm$^2$. The reaction can be carried out in the presence or absence of an inert gas. In the former case, nitrogen, hydrogen, ammonia, carbon dioxide, or the like can be used as the inert gas. When using the inert gas, it is preferred to previously introduce the inert gas into the reaction system to a pressure of about 0 to 50 kg/cm$^2$.

The starting materials, anilines and 1,2-glycols, used in the present invention need not be of high purity. Aniline, for example, may contain small amounts of nitrobenzene and phenol, which are commonly contained in the aniline. Ethylene glycol may contain, for example, acetic acid and polyethylene glycol. In addition, other hydrocarbons and their derivatives may be contained as long as they do not exert adverse influences on the reaction.

As the reaction proceeds, water is formed. If water is present in the reaction system from the beginning, the yield may be somewhat decreased. For this reason, it is preferred for the starting materials not to contain water.

In the process of the present invention, the mole ratio of the 1,2-glycols to the anilines in the reaction system is 0.01:1 to 5:1 and preferably 0.02:1 to 2:1. The amount of the catalyst used is, as calculated as $CdX_2^1$, at least 0.001 mole, preferably 0.01 to 10 moles, and more preferably 0.05 to 0.5 mole per mole of the 1,2-glycols. The reaction temperature is 200° to 500° C. and preferably 250° to 400° C.

After the reaction, most of the catalyst is removed by conventional techniques such as filtration. The catalyst thus separated was reused for the reaction. The remaining solution is subjected to distillation, for example, to recover unused starting materials, unused anilines and 1,2-glycols. These unused starting materials are reused for the reaction. Then the desired product, indoles, and the like are separated by distillation, for example, and purified. The catalyst from the residue is recovered by conventional techniques such as filtration, and the catalyst thus recovered is combined with the above catalyst and reused for the reaction.

The above procedure is given as one example of the process of the present invention, and the present invention is, of course, not limited thereto.

In the separation and washing of the catalyst, solvents such as carbon tetrachloride, chloroform, dichloromethane, dichloroethane, and toluene can be used. The recovered catalyst may be used as it is. If desired, the recovered catalyst may be used after washing with the above solvent or after regenerating by calcination, for example, in the air.

When the reaction is carried out in the presence of a diluent having a boiling point higher than that of the indoles to be prepared, operations such as the separation of the catalyst can be omitted. In this case, after the reaction, the reaction mixture is subjected to distillation, for example, to recover unused starting materials and the unused starting materials thus recovered are reused for the reaction. Then the reaction product, indoles, is separated by techniques such as distillation and purified. The residual oil containing the catalyst and the diluent having a boiling point higher than that of the desired product is reused for the reaction, if desired, after addition of a fresh catalyst and/or a fresh diluent.

The above procedure is given for illustration, and the present invention is, of course, not limited thereto. In accordance with this procedure, the catalyst does not cause problems such as deposition and coagulation and can be easily reused while maintaining its high activity.

The present invention is described in greater detail with reference to the following examples.

EXAMPLE 1

A 100 ml stainless steel autoclave with a stirrer and lined with Hastelloy was charged with 48.0 g (0.52 mole) of aniline, 3.2 g (0.052 mole) of ethylene glycol, 2.9 g (0.0107 mole) of anhydrous cadmium bromide (obtained by dehydration of $CdBr_2 \cdot 4H_2O$ (guaranteed regent manufactured by Wako Pure Chemical Industry Co., Ltd.)), and 3.7 g (0.0311 mole) of potassium bromide (guaranteed reagent manufactured by Wako Chemical Industry Co., Ltd.). After replacement of the atmosphere in the autoclave with hydrogen gas, the hydrogen gas was introduced at a pressure of 15 kg/cm$^2$ and, thereafter, the reaction was carried out with stirring at a temperature of 330° C. As the reaction proceeded, hydrogen gas and steam were formed, which added to increase in the pressure in the autoclave. The reaction was deemed completed when the increase in the pressure stopped. The reaction time was 1.2 hours.

After the reaction, the catalyst was removed from the reaction mixture by filtration. The reaction products were analyzed by gas chromatography. The product was isolated by distillation. Based on its melting point and IR, $^1$H-NMR and $^{13}$C-NMR analyses, the product was confirmed as indole.

The results were as follows:
Amount of indole: 4.5 g
Conversion based on ethylene glycol: 99.8%
Indole selectivity based on ethylene glycol: 76.2%
Indole selectivity based on aniline: 81.8%
Yield of indole based on ethylene glycol: 76.0%
By-products were formed only in small amounts.

EXAMPLE 2

The procedures of Example 1 were repeated except that the amount of potassium bromide was changed to 1.2 g and the reaction time was changed to 1.4 hours.
Conversion based on ethylene glycol: 99.5%
Indole selectivity based on ethylene glycol: 66.6%
Indole selectivity based on aniline: 75.4%
Yield of indole based on ethylene glycol: 66.3%

EXAMPLE 3

The procedures of Example 1 were repeated except that 3.8 g of cadmium iodide and 1.7 g of potassium iodide were used, and the reaction time was changed to 1.5 hours.
Conversion based on ethylene glycol: 99.8%
Indole selectivity based on ethylene glycol: 63.9%
Indole selectivity based on aniline: 75.4
Yield of indole based on ethylene glycol: 63.8%

EXAMPLE 4

The procedures of Example 1 were repeated except that 3.8 g (0.0104 mole) of cadmium iodide and 5.2 g (0.0313 g) of potassium iodide were used, and the reaction time was changed to 1.5 hours.
Conversion based on ethylene glycol: 99.6%
Indole selectivity based on ethylene glycol: 67.5%
Indole selectivity based on aniline: 80.6%
Yield of indole based on ethylene glycol: 67.3%

EXAMPLE 5

The procedures of Example 1 were repeated except that the amount of potassium bromide was changed to 5.0 g, and the reaction time was changed to 1.9 hours.
Conversion based on ethylene glycol: 99.5%
Indole selectivity based on ethylene glycol: 71.2%
Indole selectivity based on aniline: 82.0%
Yield of indole based on ethylene glycol: 70.8%

EXAMPLE 6

Cadmium bromide was added to an aqueous potassium bromide solution (mole ratio of cadmium bromide to potassium bromide: 1:1) and stirred for 3 hours while heating at 80° to 90° C. The resulting solution was concentrated under reduced pressure, and solids precipitated were washed with water to obtain $KCdBr_3$ crystals.

Thereafter, the procedures of Example 1 were repeated except that 4.2 g (0.0107 mole) of $KCdBr_3$ was used in place of the cadmium bromide and potassium bromide, and the reaction time was changed to 1.4 hours.
Conversion based on ethylene glycol: 99.4%
Indole selectivity based on ethylene glycol: 65.1%
Indole selectivity based on aniline: 83.0%
yield of indole based on ethylene glycol: 64.7%

EXAMPLE 7

The procedures of Example 1 were repeated except that o-toluidine was used in place of aniline and the reaction time was changed to 1.7 hours.
Conversion based on ethylene glycol: 99.7%
7-Methylindole selectivity based on ethylene glycol: 79.0%
7-Methylindole selectivity based on aniline: 83.2%
Yield of 7-methylindole based on ethylene glycol: 78.8%

EXAMPLE 8

The procedures of Example 1 were repeated except that the amount of aniline used was changed to 24.0 g (0.26 mole) and the reaction time was changed to 2 hours.
Conversion based on ethylene glycol: 99.8%
Indole selectivity based on ethylene glycol: 69.3%
Indole selectivity based on aniline: 82.5%
Yield of indole based on ethylene glycol: 69.2%

COMPARATIVE EXAMPLES 1 TO 9

The procedures of Example 1 were repeated except that the catalysts as shown in Table 1 were used, and the reaction time was changed as shown in Table 1.
The results are shown in Table 1.

TABLE 1

| Comparative Example | Catalyst (g) | | Reaction Time (hr) | Ethylene Glycol Conversion (%) | Indole Selectivity Based on Ethylene Glycol (%) | Indole Selecitivity Based on Aniline (%) | Yield of Indole (%) |
| --- | --- | --- | --- | --- | --- | --- | --- |
| 1 | CdF$_2$ (1.6) | — | 3.3 | 12.5 | 55.2 | 69.2 | 6.9 |
| 2 | CdF$_2$ (1.6) | KF (1.8) | 3.6 | 4.9 | 10.2 | 13.9 | 0.5 |
| 3 | CdCl$_2$ (1.9) | — | 1.8 | 99.2 | 51.9 | 49.4 | 51.5 |
| 4 | CdCl$_2$ (1.9) | KCl (0.8) | 2.1 | 98.9 | 49.4 | 62.1 | 48.9 |
| 5 | CdCl$_2$ (1.9) | KCl (2.4) | 1.5 | 67.7 | 62.5 | 73.2 | 42.3 |
| 6 | CdBr$_2$ (2.9) | — | 1.8 | 99.2 | 62.6 | 54.6 | 62.0 |
| 7 | CdBr$_2$ (2.9) | KCl (2.4) | 1.9 | 99.5 | 50.7 | 73.3 | 50.5 |
| 8 | CdI$_2$ (3.8) | — | 1.5 | 97.5 | 54.6 | 46.5 | 53.2 |
| 9 | — | KCl (3.9) | 2.6 | 15.4 | 55.8 | 67.3 | 8.6 |

EXAMPLE 9

The procedures of Example 1 were repeated except that the residue resulting from the removal by distillation of excess aniline and formed indole from the reaction mixture obtained in Example 1 was used as the catalyst, and the reaction time was changed to 1.3 hours.

Conversion based on ethylene glycol: 99.6%
Indole selectivity based on ethylene glycol: 73.15
Indole selectivity based on aniline: 84.9%
Yield of indole based on ethylene glycol: 72.8%

From the reaction mixture thus formed was recovered the catalyst in the same manner as above, and the reaction was again conducted using the recovered catalyst. The following results were obtained.

Conversion based on ethylene glycol: 98.9%
Indole selectivity based on ethylene glycol: 73.0%
Indole selectivity based on aniline: 84.5%
Yield of indole based on ethylene glycol: 72.2%

EXAMPLE 10

A 100 ml stainless steel autoclave with a stirrer and line with Hastelloy was charged with 24.8 g (0.27 mole) of aniline, 3.3 g (0.053 mole) of ethylene glycol, 2.9 g (0.011 mole) of anhydrous cadmium bromide, 3.8 g (0.032 mole) of potassium bromide, and 16.5 g of a liquid paraffin, Daphne Oil CP-32N (manufactured by Idemitsu Kosan Co., Ltd.). The atmosphere in the autoclave was replaced by nitrogen gas and then the nitrogen gas was introduced under a pressure of 5 kg/cm$^2$. Thereafter the reaction was carried out at a temperature of 300° C. while stirring. The boiling point distribution of the liquid paraffin is shown in Table 2. As the reaction proceeded, the pressure in the autoclave increased under the action of formed hydrogen gas and steam. The reaction was deemed completed when the increase in the pressure stopped. The reaction time was 2.7 hours.

After the reaction, the catalyst was removed from the reaction mixture by filtration, and the reaction products were analyzed by gas chromatography. The products were isolated by distillation. The formation of indole was confirmed by measuring the melting point and analyzing Mass spectrum, $^1$H-NMR, $^{13}$C-NMR, and IR spectra. The boiling point of the indole was less than 160° C. (10 mmHg). The amount of the obtained indole was 5.0 g.

Conversion based on ethylene glycol: 99.3%
Indole selectivity based on ethylene glycol: 82.6%
Selectivity based on aniline: 95.6%
Yield of indole based on ethylene glycol: 82.0%

The amounts of by-products were very small, and only small amounts of methylquinoline and 1,2-dianilinoethane were detected.

TABLE 2

| Condition of Distillation | Distillation Temperature at 10 mmHg Liquid Paraffin | |
| --- | --- | --- |
| | Daphne Oil CP32N (°C.) | Daphne Oil CP15N (°C.) |
| Initial Point | 206 | 160 |
| 5% | 229 | 179 |
| 10% | 238 | 183 |
| 20% | 253 | 199 |
| 30% | 262 | 213 |
| 40% | 271 | 228 |
| 50% | 278 | 244 |
| 60% | 285 | 260 |
| 70% | 293 | 277 |
| 80% | 301 | 293 |
| 90% | 312 | 308 |
| 95% | 325 | 320 |
| 97% | 336 | 332 |
| End Point | 348 | 346 |

EXAMPLE 11

The procedures of Example 10 were repeated except that the amount of the liquid paraffin used was changed to 34.5 g.

Conversion based on ethylene glycol: 99.1%
Indole selectivity based on ethylene glycol: 82.2%
Yield of indole based on ethylene glycol: 81.5%

EXAMPLE 12

The procedures of Example 10 were repeated except that 16.5 g of Daphne Oil CP-15 N (manufactured by Idemitus Kosan Co., Ltd.) was used as the liquid paraffin, and the reaction time was changed to 2.8 hours.

Conversion based on ethylene glycol: 99.0%
Indole selectivity based on ethylene glycol: 81.0%
Yield of indole based on ethylene glycol: 80.2%

The boiling point distribution of the liquid paraffin is shown in Table 2.

EXAMPLE 13

The procedures of Example 10 were repeated except that the amount of the aniline used was changed to 19.8 g (mole ratio of aniline to ethylene glycol: 4:1), and the reaction time was changed to 2.2 hours.

Conversion based on ethylene glycol: 99.2%
Indole selectivity based on ethylene glycol: 74.1%
Yield of indole based on ethylene glycol: 73.5%

EXAMPLE 14

The procedures of Example 10 were repeated except that 3.7 g (0.010 mole) of cadmium iodide and 5.0 g (0.030 mole) of potassium iodide were used as the catalyst, and the reaction time was changed to 2.3 hours. The following results were obtained.
Conversion based on ethylene glycol: 98.7%
Indole selectivity based on ethylene glycol: 73.3%
Yield of indole based on ethylene glycol: 72.3%

EXAMPLE 15

In Example 10, after the reaction was completed, the contents in the autoclave (except for the gas component) was transferred to a flask. The reaction products and starting materials were distilled away at a pressure of 10 mmHg and a temperature of 160° C., thereby leaving the liquid paraffin and the catalyst in the bottom of the flask.

The liquid paraffin/catalyst mixture was transferred to the autoclave and fresh starting materials were added. The reaction was carried out under the same conditions as in Example 10. The yield of indole based on ethylene glycol was 83.0%.

The above procedures were repeated six times. In each case, the yield was as high as more than 80%, and the liquid paraffin/catalyst mixture was in a liquid form and the deposition of the catalyst did not occur at all.

While the invention has been described in detail and with reference to specific embodiments thereof, it will be apparent to one skilled in the art that various changes and modifications can be made therein without departing from the spirit and scope thereof.

What is claimed is:

1. A process for producing an indole compound, comprising:
   reacting an aniline compound of the formula:

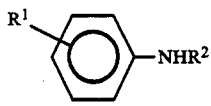

wherein $R^1$ is hydrogen, $C_{1-4}$ alkyl, $C_{1-4}$ alkoxy, hydroxy, halogen or nitro, and $R^2$ is hydrogen or $C_{1-4}$ alkyl and a 1,2-glycol compound of the formula:

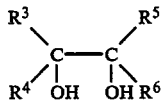

wherein $R^3$-$R^6$, are the same or different, and each represents hydrogen, $C_{1-4}$ alkyl or $C_{1-4}$ alkyl substituted by halogen, hydroxy or cyano in a liquid phase in the presence of a catalyst comprising $CdX_2^1$ and $KX^2$, wherein $X^1$ and $X^2$, are the same or different, and each represents bromine or iodine.

2. The process as claimed in claim 1, wherein the mole ratio of $KX^2$ to $CdX_2^1$ is 0.1:1 to 10:1.

3. The process as claimed in claim 2, wherein the mole ratio of $KX^2$ to $CdX_2^1$ is 1:1 to 7:1.

4. The process as claimed in claim 3, wherein the mole ratio of $KX^2$ to $CdX_2^1$ is 2:1 to 5:1.

5. The process as claimed in claim 1, wherein the amount of the catalyst used, calculated as $CdX_2^1$, is at least 0.001 mole per mole of said 1,2-glycol compound.

6. The process as claimed in claim 5, wherein the amount of the catalyst used, calculated as $CdX_2^1$, is 0.01 to 10 mole per mole of said 1,2-glycol compound.

7. The process as claimed in claim 6, wherein the amount of the catalyst used, calculated as $CdX_2^1$, is 0.05 to 0.5 mole per mole of said 1,2-glycol compound.

8. The process as claimed in claim 1, wherein the mole ratio of the 1,2-glycol compound to the aniline compound is 0.01:1 to 5:1.

9. The process as claimed in claim 8, wherein the mole ratio of the 1,2-glycol compound to the aniline compound is 0.02:1 to 2:1.

10. The process as claimed in claim 1, wherein the reaction is carried out at a temperature of 200° to 500° C.

11. The process as claimed in claim 10, wherein the reaction is carried out at a temperature of 250° to 400° C.

12. The process as claimed in claim 1, wherein the reaction is carried out at atmospheric pressure or under superatmospheric pressure.

13. The process as claimed in claim 12, wherein the reaction is carried out at a pressure of 0 to 200 kg/cm$^2$.

14. The process as claimed in claim 1, wherein the reaction is carried out in the presence of a diluent.

15. The process as claimed in claim 1, wherein the diluent is a saturated hydrocarbon, an aromatic hydrocarbon or an organic solvent.

16. The process as claimed in claim 15, wherein the diluent is selected from the group consisting of paraffin, naphthene, benzene, toluene, xylene, trimethylamine, triphenylamine, dioxane, dimethylformamide, dimethyl sulfoxide, pyridine, and N-methylpyrrolidone.

17. The process as claimed in claim 14, wherein the diluent has a boiling point higher than that of the indole to be prepared.

18. The process as claimed in claim 17, wherein the diluent is a saturated hydrocarbon.

19. The process as claimed in claim 18, wherein the saturated hydrocarbon is a liquid paraffin.

20. The process as claimed in claim 18, wherein the weight ratio of the liquid saturated hydrocarbons to the aniline compound is 0.01:1 to 100:1.

21. The process as claimed in claim 20, wherein the weight ratio of the liquid saturated hydrocarbons to the aniline compound is 0.1:1 to 10:1.

22. The process as claimed in claim 1, wherein the 1,2-compound is selected from the group consisting of ethylene glycol, propylene glycol, 1,2-butanediol, 2,3-butanediol, pinacol, glycerol, glycerol-2-monochlorohydrin, and glycerol-2-monocyanohydrin.

23. The process as claimed in claim 1, wherein the 1,2-glycol compound is ethylene glycol and contains a polyethylene glycol in an amount of 50 wt% or less based on the weight of the ethylene glycol.

24. The process as claimed in claim 1, wherein the catalyst contains an additive selected from the group consisting of halides, sulfides, sulfates and oxides of metals selected from the group consisting of B, Al, In, Sn, Ti, V, Cr, Si, Mn, Fe, Co, Ni, Cu, Zn, Zr, Mo, Ru, Rh, Pd, Ag, Re, Os, Ir, Pt, Hg, La, Ce, Nd, Na, Li, Rb, Cs, Be, Mg, Ca, Sr, Ba, Pb, Tl, Bi and G, and activated carbon.

25. The process as claimed in claim 1, wherein the catalyst is added as a compound of the formula: $K_aCdX_{(2+a)}$, wherein X is bromine, iodine, or a mixture thereof and a is an integer of 1 to 4, said compound having previously been prepared from the cadmium compound $CdX_2^2$ and potassium compound $KX^2$.

* * * * *